United States Patent [19]

Quimby

[11] Patent Number: 4,776,690

[45] Date of Patent: Oct. 11, 1988

[54] METHOD AND REAGENT GAS FOR THE ANALYSIS OF NITROGEN-CONTAINING COMPONENTS USING ATOMIC EMISSION SPECTROMETRY

[75] Inventor: Bruce D. Quimby, Landenberg, Pa.

[73] Assignee: Hewlett-Packard Company, Palo Alto, Calif.

[21] Appl. No.: 105,437

[22] Filed: Oct. 5, 1987

[51] Int. Cl.[4] ............................................. G01N 21/73
[52] U.S. Cl. ...................................... 356/72; 356/316; 436/115; 436/160
[58] Field of Search ..................... 356/72, 315, 316; 436/114, 115, 160, 171

[56] References Cited

U.S. PATENT DOCUMENTS 4,467,038  8/1984  Scott ................................. 436/115

Primary Examiner—Vincent P. McGraw
Attorney, Agent, or Firm—Frank R. Perillo; Patrick J. Barrett

[57] ABSTRACT

The nitrogen-selectivity of an atomic emission detection system is enhanced by use, as the reagent gas, of a single gas or a mixture of gas components containing oxygen and hydrogen in an oxygen/hydrogen molar ratio of about 1:10 to 10:1.

23 Claims, 2 Drawing Sheets

METHOD AND REAGENT GAS FOR THE ANALYSIS OF NITROGEN-CONTAINING COMPONENTS USING ATOMIC EMISSION SPECTROMETRY

BACKGROUND OF THE INVENTION

The present invention relates to the use of atomic emission spectrometry for the element-specific analysis of a sample, preferably a fractionated sample eluted from a separation means such as a gas chromatograph. More particularly, the invention relates to the use of an improved reagent (or scavenger) gas which provides increased selectivity for nitrogen detection.

Atomic emission spectrometers equipped with plasma-excitation means are commonly used in many applications of chemical analysis for quantitative determination of the presence of particular elements in a multicomponent sample. The spectrometers are also used in the analysis of the fractionated effluent from a separatory device such a gas chromatograph (GC). In that function, the atomic emission line for the desired element is monochromatically monitored and plotted as a function of time, correlatable with the period of time over which the various components of the fractionated sample pass through the plasma-forming stage of the spectrometer. The utility of this analytical technique, particularly in such applications as the monitoring of environmental pollutants, is critically dependent on the use of a spectrometer that is highly element-selective.

As used herein, the "selectivity" of an atomic emission spectrometer or detector (AED) is the ability of the detector to reject a response from compounds not containing the specific element of interest. Selectivity is normally expressed as the ratio of the mass of a compound not containing the selected element necessary to produce the same chromatographic response as a mass of a compound that does contain that element.

The selectivity in atomic emission spectrometry is as high as 10,000 for most elements, provided the specific detector used has sufficiently high resolution and is capable of filtering spectral background "noise" (interfering signals from, for example, molecular emissions). The selectivity for nitrogen, however, has been considerably lower than this with the analytical equipment and methods of the prior art. For example, in atomic emission spectrometry using atmospheric pressure microwave-induced helium plasma, nitrogen has exhibited a selectivity which is often no higher than about 50, which is too low to allow proper distinction between nitrogenated and non-nitrogenated hydrocarbons.

Improvements in the results available for atomic emission spectrometry in general have been made through the use of reagent (or scavenger) gases, which are usually injected into the stream of carrier gas (generally helium) which entrains the sample just before the inlet to the spectrometer. Reagent gases, which are generally injected in amounts of about 0.05-2.0 volume percent of the total gas, are used to prevent the deposition of soot on the lamp or discharge tube, which is a particular problem when carbon or sulfur compounds are in the sample to be analyzed. The most commonly used reagent gases have been oxygen, hydrogen, and nitrogen, the choice of the particular reagent for use being dependent upon its absence in the sample compounds of interest to avoid the production of background noise. U.S. Pat. No. 3,887,208, for example, discloses the individual use of each of these gases in the elemental analysis of a carbon-containing sample.

In the particular case of the detection of nitrogen-containing compounds, however, the use of reagent gases has not significantly improved the nitrogen-to-carbon selectivity. The prior art's use of oxygen or hydrogen individually as the reagent gas during analysis for nitrogenated compounds has not been able to eliminate the chromatographic responses of the non-nitrogenated compounds at the nitrogen wavelength. Accordingly, there remains a need for atomic emission spectrometry having improved selectivity for nitrogen.

SUMMARY OF THE INVENTION

The present invention provides an improved method of elemental analysis of a sample which includes a nitrogen-containing compound. The basic method comprises the steps of (i) introducing a mixture of the sample, an inert carrier gas therefor, and a reagent gas into an atomic emission spectrometer having plasma-excitation means; (ii) forming a plasma from said mixture, and (iii) detecting at least one nitrogen or nitrogen-related optical emission generated in the spectrometer. The improvement provided by the present invention is characterized in that the reagent gas is a single gas or mixture of gases containing the elements oxygen and hydrogen in an oxygen/hydrogen molar ratio of about 1:10 to 10:1. In preferred embodiments, the reagent gas is a mixture of oxygen gas and hydrogen gas themselves; water vapor alone; or mixtures of either oxygen gas or hydrogen gas with water vapor.

The method of the present invention substantially enhances the capability to selectively detect nitrogenated compounds, the importance thereof being highlighted by the fact that nitrogen is one of the most prevalent elements in industrially, biologically, and medically important organic and inorganic compounds. A further advantage of the present invention is its applicability to existing equipment for atomic emission detection. No substantial modification of such equipment is necessary, and the invention can otherwise be practiced, and its benefits achieved, with standard spectrometers.

BRIEF DESCRIPTION OF THE DRAWINGS

FIG. 1b is a sulfur-specific chromatogram, using oxygen as a reagent gas, of the sample of FIG. 1a.

FIG. 1c is a nitrogen-specific chromatogram, using oxygen as a reagent gas, of the sample of FIG. 1a.

DETAILED DESCRIPTION OF THE INVENTION

Figure 1A:
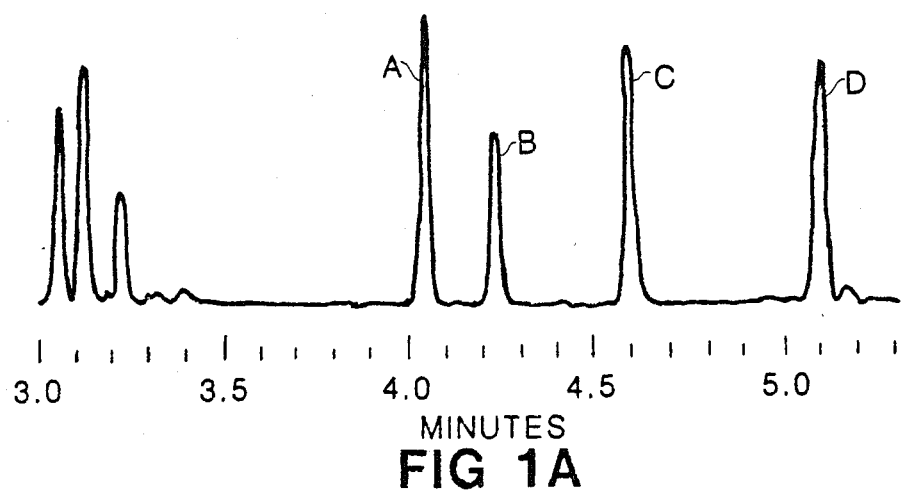
FIG. 1a is a carbon-specific chromatogram, using oxygen as a reagent gas, of a fractionated sample of known composition.

The present invention provides an improvement in the use of atomic emission spectrometry for chemical analysis by which the nitrogen selectivity of the analysis is greatly enhanced. More particularly, the invention is based on the improved nitrogen selectivity obtained by the use of a mixture of hydrogen and oxygen as the reagent gas that normally accompanies the sample into the plasma-forming chamber of thespectrometer. The present invention is based in part on the finding that the spectrometer's nitrogen channel response to non-nitrogenated compounds is proportional to the hydrogen content of the compound. It has now been found that the use in the reggent gas of hydrogen, as a buffer for the hydrogen content of the sample, in conjunction with oxygen provides surprisingly better nitrogen selectivety than does the use of either of these gases individually, as has been the practice heretofore.

In the performance of atomic-emission analyses of the kind to which the present invention pertains, the sample to be analyzed and a carrier gas for that sample are directed into an atomic emission spectrometer equipped with apparatus to generate a plasma from the carrier gas and sample. The invention is particularly useful in the analysis of the fractionated effluent from a separatory device such as a gas chromatograph (GC), and the invention will hereafter be described in terms of this preferred embodiment, although it is to be understood that it is equally applicable to the analysis of an unfractionated single-component or unfractionated multi-component sample as well. When such a separatory device is used, its effluent is directed into an atomic emission spectrometer equipped to generate a plasma from the effluent. By means of the spectrometer, the atomic emission line of the desired element within the sample is monitored and generally correlated with the passage of the various compounds contained in the fractionated sample through the plasma-forming stage of the spectrometer. Carrier gases that are in general use are inert gases such as helium, argon, and neon. The plasma can be generated by subjecting the gas to, for example, microwave radiation. Microwave induction of helium plasma is preferred according to the present invention.

In general practice, the hardware connection between the gas-separation device and the spectrometer is generally equipped with means for introducing additional carrier gas (known as make-up gas) and a reagent gas into the effluent of the separatory device prior to that stream's entering the spectrometer. Although these gases can be introduced into the effluent through separate ports in the effluent line, they are usually and preferably pre-combined in a common feed line and injected through a single port. The make-up gas is used primarily to maintain the effluent pressure sufficiently above atmospheric pressure to provide proper flow to the spectrometer, the plasma-forming step of which is preferably at or just above atmospheric pressure. The reagent gas and make-up gas can each be bled into the common feed line through, for example, an adjustable pressure valve or controller.

In general practice and for purposes of the present invention, flow rates of the sample plus carrier gas through a gas chromatograph vary from as little as about 0.5 ml/min (calculated at standard conditions) to as much as about 50 ml/min. The make-up gas is added to the column effluent in an amount of about 10-50 ml/min to provide a v/v ratio with the effluent in the range of about 1.0-20.0. The reagent gas is generally added in an amount sufficient to provide about 0.05-2.0 volume percent, preferably about 0.1-1.5 volume percent, of the total gas entering the plasma.

According to the present invention, the nitrogen selectivity of an analytical system of the kind described above is enhanced when the reagent gas consists essentially of oxygen and hydrogen. That is, the reagent gas used is a single gas component or mixture of gas components containing the elements oxygen and hydrogen in an oxygen/hydrogen molar ratio of about 10:1 to 1:10. Preferably, the reagent gas is a mixture of oxygen gas and hydrogen gas themselves, water vapor alone, or mixtures of oxygen gas or hydrogen gas with water vapor. Other gases containing oxygen, hydrogen, or both (and preferably no other elements) can also be used as all or part of the reagent gas. Examples are ozone and hydrogen peroxide. Most preferably, a mixture of oxygen gas and hydrogen gas alone is used.

The various components of the reagent gas are provided in amounts constituting an oxygen-to-hydrogen molar ratio of about 1:10 to about 10:1, preferably 1:5 to 10:1, and most preferably about 1:1 to 5:1. Water vapor alone, for example, provides an oxygen/hydrogen ratio of 1:2. An equimolar mixture of water vapor and oxygen (as $O_2$) provides an oxygen/hydrogen ratio of 1.5:1.

In operation, the improved reagent gas can be introduced into the mixture from which the plasma is to be generated at any point in the system. It is important only that the flow and composition of the reagent gas be controlled to be within the effective range. Most preferably, the reagent gas is added with the make-up gas by separately metering and bleeding those gases into a common feed line as earlier described. Any conventional means for metering the flow of gas, such as those combining adjustable pressure controllers and flow restrictors, can be used so long as the flow of the oxygen-hydrogen reagent gas is controllable and can be maintained within the effective concentration.

The present invention is illustrated by reference to FIGS. 1 and 2, which depict a comparative study of the chromatograms generated by a known sample mixture both with and without the improved reagent gas. The mixture on which the study was conducted consisted of nitro-benzene (Compound "A" in the figures), t-butyl disulfide ("B"), n-dodecane ("C"), and n-tridecane ("D") in a carrier gas of helium. Apparatus used in the study included a Hewlett Packard 5890A Gas Chromatograph with dedicated on-column injection, and a laboratory-built spectrometer having a 0.5 m, f/8 concave grating mount and equipped with a solvent-dumping means as described in U.S. Pat. No. 4,517,824. Operating conditions for the GC-AED study are summarized in the following table.

| GC-AED Operating Conditions | |
| --- | --- |
| Chromatographic Conditions | |
| Column | 12 m cross-linked 5% phenyl methyl silicon (0.53 mm I.D.; 0.88 μm film thickness) |
| Helium flow-rate | 8 ml/min (research grade purity) |
| Injection size | 1 μl |
| Column temperature | 65° C. to 200° C. at 10° C./min (programmed) |
| Detection interface temperature | 250° C. |
| Spectroscopic Conditions | |
| Microwave plasma cavity | Modified $TM_{010}$ (with water-cooled discharge tube) at atmospheric pressure |
| Tuning device | Coaxial stubstretcher |
| Power | 120 W at 2450 MHz |
| Helium flow-rate | 50 ml/min (8 ml/min from column; 42 ml/min make-up) |

| GC-AED Operating Conditions | |
|---|---|
| Reagent gas flow-rate | 0.5 ml/min |
| Element detection wavelength | |
| Nitrogen | 174.2 nm |
| Carbon | 193.1 nm |
| Sulfur | 180.7 nm |
| Spectral resolution | 0.075 nm |
| Entrance slit | 60.0 μm (width) by 5 mm (height) |
| Computer | Hewlett Packard Model 9836 |
| Plotter | Hewlett Packard Model 2673A |
| Photodetector | 212 pixel linear photodiode array, pixel size 60 × 600 μm |

Figure 1B:
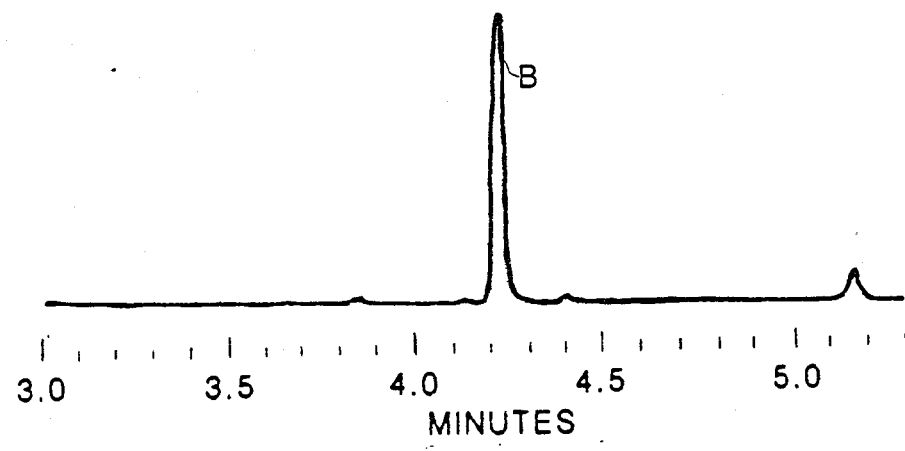

FIG. 1a is a carbon chromatogram of the sample mixture and FIG. 1b is a sulfur chromatogram of the same mixture taken simultaneously at the sulfur-detection wavelength. The reagent gas used in the generation of each of these control chromatograms was oxygen, about 0.5% by volume of total gas. As can be seen, all compounds, as expected, generate sharp responses at the carbon wavelength (FIG. 1a). (The oompounds eluting at about 3.0–3.3 minutes were impurities from the original solvent.) The selectivity for the sulfur channel is shown in FIG. 1b also to be excellent, the only response being to the single sulfur-containing compound (B); there is no detectable response from any of the non-sulfur containing compounds in the mixture.

Figure 1C:
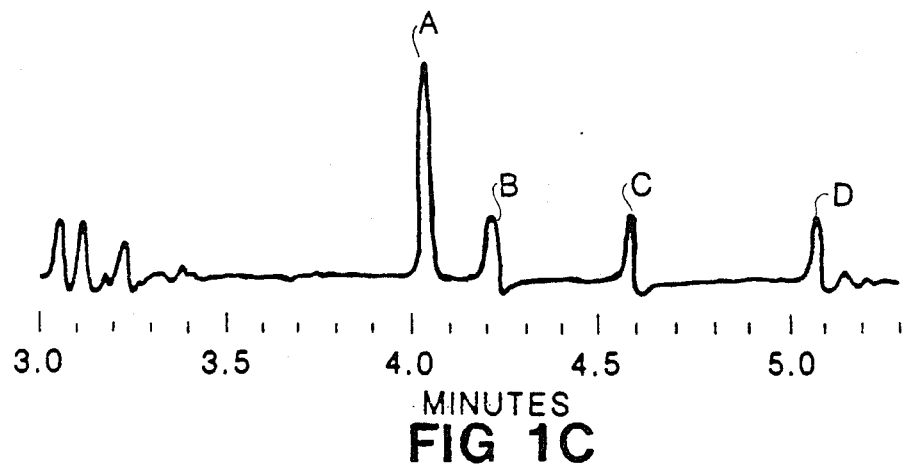

FIG. 1c is the nitrogen chromatogram for the test mixture plotted at the nitrogen wavelength, again using oxygen as the reagent gas at a concentration of about 0.5% by volume (corresponding to a rate of about 0.5 ml/min) of the total helium entering the detector. This control chromatogram demonstrates the poor nitrogen selectivity of existing spectrometry methods; all compounds in the mixture produce significant responses, with some zig-zag peak tails.

Figure 2A:
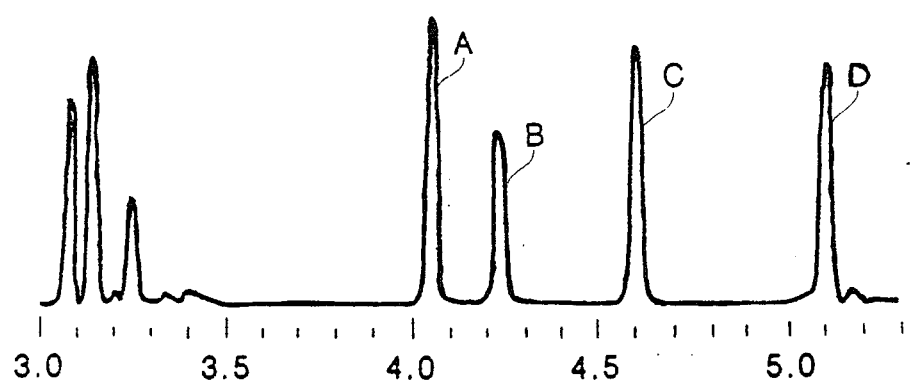
FIG. 2a is a carbon-specific chromatogram of the sample of FIG. 1a using a 5:1 v/v mixture of oxygen gas and hydrogen gas as the reagent gas.
Figure 2B:
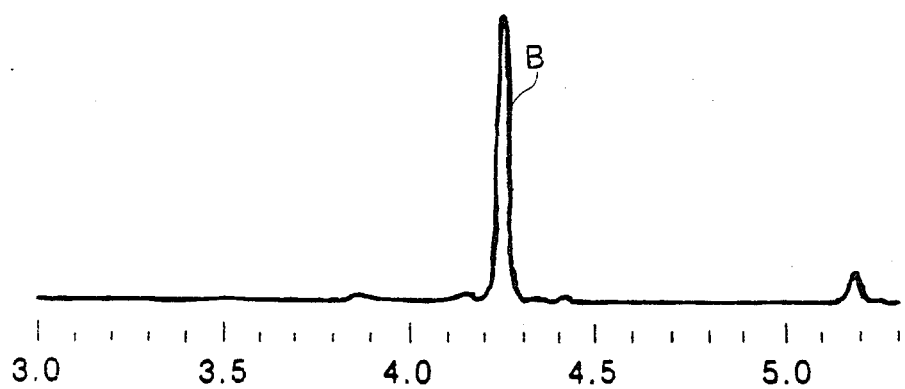
FIG. 2b is a sulfur-specific chromatogram of the 15 sample of FIG. 1b using a 5:1 v/v mixture of oxygen gas and hydrogen gas as the reagent gas.
Figure 2C:
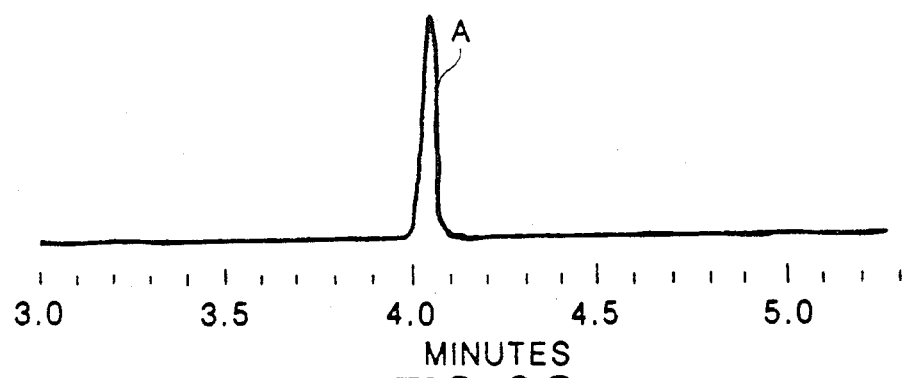
FIG. 2c is a nitrogen-specific chromatogram of the sample of FIG. 1c using a 5:1 v/v mixture of oxygen gas and hydrogen gas as the reagent gas.

The use of the improved reagent gas of the present invention is shown in FIGS. 2a–c. These chromatograms depict analyses of the same sample mixture of FIGS. 1a–c, but with use as the reagent gas of a mixture of oxygen and hydrogen in a v/v ratio of about 5:1 (with an overall reagent gas concentration of about 0.6% by volume of the total gas reaching the plasma. FIGS. 2a and 2b, the carbon and sulfur chromatograms, respectively, are unchanged. In the nitrogen chromatogram, FIG. 2c, the response to the single nitrogenated target compound of the mixture, Compound A, is positive and strong. Comparison to FIG. 1c shows that responses to the non-nitrogenated target compounds are substantially reduced o eliminated.

What is claimed is:

1. An improved method of elemental analysis of a sample which includes a nitrogen-containing compound of the kind comprising the steps of (i) introducing a mixture of the sample, an inert carrier gas therefor, and a reagent gas into an atomic emission spectrometer having plasma-excitation means, (ii) forming a plasma from said mixture, and (iii) detecting at least one nitrogen or nitrogen-related optical emission generated thereby, wherein the improvement is characterized in that the reagent gas consists essentially of oxygen and hydrogen in an oxygen/hydrogen molar ratio of about 1:10 to 10:1.

2. The method of claim 1 in which the reagent gas is a single gas component or a mixture of gas components containing oxygen and hydrogen.

3. The method of claim 2 in which the reagent gas consists essentially of a mixture of oxygen gas and hydrogen gas alone.

4. The method of claim 2 in which the reagent gas is water vapor.

5. The method of claim 2 in which the reagent gas consists essentially of a mixture of water vapor with oxygen gas, hydrogen gas, or a combination of oxygen gas and hydrogen gas.

6. The method of claim 5 in which the reagent gas consists essentially of a mixture of water vapor and oxygen gas.

7. The method of claim 1 in which the oxygen/hydrogen ratio is about 1:5 to 10:1.

8. The method of claim 1 in which the oxygen/hydrogen ratio is about 1:1 to 5:1.

9. The method of claim 3 in which the oxygen/hydrogen ratio is about 1:5 to 10:1.

10. The method of claim 3 in which the oxygen/hydrogen ratio is about 1:1 to 5:1.

11. The method of claim 5 in which the oxygen/hydrogen ratio is about 1:5 to 10:1.

12. The method of claim 5 in which the oxygen/hydrogen ratio is about 1:1 to 5:1.

13. The method of claim 6 in which the oxygen/hydrogen ratio is about 1:1 to 5:1.

14. The method of claim 1 in which the sample has been fractionated in a gas chromatograph.

15. The method of claim 14 in which the carrier gas is helium and the plasma is formed by microwave induction at atmospheric pressure.

16. The method of claim 3 in which the sample has been fractionated in a gas chromatograph.

17. The method of claim 16 in which the carrier gas is helium and the plasma is formed by microwave induction at atmospheric pressure.

18. The method of claim 4 in which the sample has been fractionated in a gas chromatograph.

19. The method of claim 18 in which the carrier gas is helium and the plasma is formed by microwave induction at atmospheric pressure.

20. The method of claim 5 in which the sample has been fractionated in a gas chromatograph.

21. The method of claim 20 in which the carrier gas is helium and the plasma is formed by microwave induction at atmospheric pressure.

22. The method of claim 10 in which the sample has been fractionated in a gas chromatograph.

23. The method of claim 22 in which the carrier gas is helium and the plasma is formed by microwave induction at atmospheric pressure.

* * * * *